Feb. 1, 1966 M. L. WHISLER Plant Pat. 2,595
ROSE PLANT
Filed Nov. 17, 1964
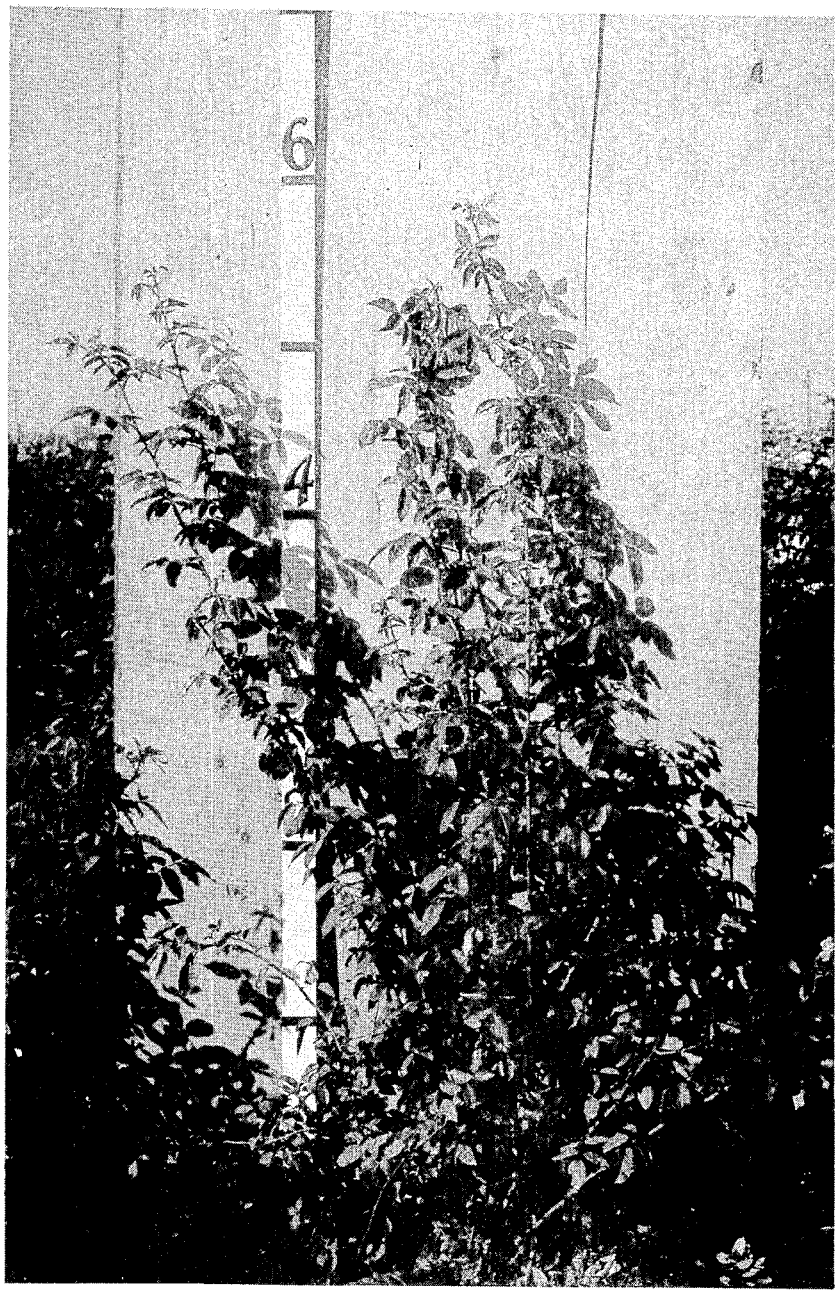
Inventor.
Milton L. Whisler
By: Robb & Robb
Attorneys.

United States Patent Office

Plant Pat. 2,595
Patented Feb. 1, 1966

2,595
ROSE PLANT

Milton L. Whisler, Shafter, Calif., assignor to Germain's, Inc., Los Angeles, Calif., a corporation of California Filed Nov. 17, 1964, Ser. No. 411,954
1 Claim. (Cl. Plt.—3)

The present invention relates to a new and distinct variety of rose plant of the climber class, which was discovered by me as a sport of the variety known as "Sun Valley" (Plant Patent No. 1,135).

At the time of my discovery aforementioned, I was in charge of the growing of a large block of plants of the regular bush rose variety "Sun Valley" in the fields of my assignee, located at Shafter, California. In the course of one of my inspections of these fields, my attention was attracted to one plant on which appeared a climbing cane. Upon close examination of this plant, I found that it had sported and I thereupon promptly took steps to preserve the sport, keep it under observation, and to asexually reproduce the same by budding, as performed at Shafter, California, for the purpose of determining whether its climbing habit was fixed and transmissible by asexual reproduction. As the result, the climbing habit was fully confirmed.

The parent variety "Sun Valley" is a popular rose variety of the regular bush type and of the hybrid tea class, but so far as I am aware, it has never previously exhibited a climbing habit and its growth has been that of the average bush rose.

The new variety is substantially identical in all respects to its parent, except that it is definitely a climber, as evidenced by its long, strong canes which attain a mature length of at least twelve feet or more. In view of the general similarities between the new sport variety and its parent, except as noted in the foregoing, it is unnecessary to specifically describe the new variety in detail herein, since it otherwise substantially conforms to the detailed description embodied in Plant Patent No. 1,135, issued September 16, 1952, to which reference may be readily had. However, for convenience, the accompanying drawing has been presented to illustrate the climbing habit of growth of the new variety.

I claim:

A new and distinct variety of rose plant of the climber class, substantially as herein shown and described, characterized particularly as to novelty by being substantially identical with its parent variety "Sun Valley" (Plant Patent No. 1,135), but being essentially distinguished therefrom by its long and strong canes which attain a mature height of at least twelve feet or more, indicative of its climbing habit of growth.

No references cited.

ABRAHAM G. STONE, *Primary Examiner.*